United States Patent
Chopra et al.

(10) Patent No.: US 6,426,062 B1
(45) Date of Patent: Jul. 30, 2002

(54) UNDERARM GEL PRODUCTS WITH WATER LOCK COMPONENT

(75) Inventors: Suman Chopra, Dayton; Jairajh Mattai, Piscataway; Lin Fei, Scotch Plains; Eric Guenin, Pennington, all of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/971,978

(22) Filed: Oct. 5, 2001

(51) Int. Cl.⁷ .............. A61K 7/32; A61K 7/34; A61K 7/36; A61K 7/38; A61K 31/79; A61K 7/00

(52) U.S. Cl. .............. 424/65; 424/66; 424/67; 424/68; 424/78.02; 424/78.08; 424/400; 424/401

(58) Field of Search .............. 424/65, 66, 67, 424/68, 78.02, 78.08, 400, 401

(56) References Cited

U.S. PATENT DOCUMENTS 5,654,362 A  8/1997  Schulz, Jr. et al.

FOREIGN PATENT DOCUMENTS

WO    WO 92/19221    11/1992

OTHER PUBLICATIONS

U.S. patent application Ser. No. 09/971,805, Chopra et al., filed Oct. 5, 2001.

*Primary Examiner*—Shelley A. Dodson
(74) *Attorney, Agent, or Firm*—Rosemary M. Miano

(57) ABSTRACT

A gelled stick or soft gel composition for reducing underarm wetness comprising: (a) 0.01–20 weight % selected from the group consisting of starch graft homopolymers and copolymers of poly(2-propenamide-co-2-propenioic acid) sodium salt; (b) 10–88 weight % of a volatile silicone; (c) a gelling agent selected from (i) a group consisting of 5–20 weight % siliconized polyamide if a gelled stick is formed; and (ii) 0–5 weight % of a siliconized polyamide and 0–5% of a silicone elastomer if a soft gel is formed; (d) 0.05–85 weight % of water or a water soluble organic solvent; (e) for products which are not sticks, 0.05–5 weight % of a surfactant with a HLB value in the range of 3–13; (f) 0–10 weight % of an antiperspirant active or an effective amount of a deodorizing agent which is not an antiperspirant active; (g) 0–20 weight % of a nonvolatile silicone; and (h) 0–20 weight % of an emollient.

20 Claims, No Drawings

UNDERARM GEL PRODUCTS WITH WATER LOCK COMPONENT

FIELD OF THE INVENTION

This invention relates to gel products that are useful to reduce underarm wetness. Optionally they can include antiperspirant and/or deodorant agents, but are particularly advantageous in providing deodorants that have reduced wetness without the use of an antiperspirant active. Reference is made to a case filed on the same day as this case and referenced as Attorney Docket Number IR 6754-00.

BACKGROUND OF THE INVENTION

A variety of technologies have attempted to use superabsorbent polymers of various types in a wide variety of applications. These technologies include the construction of diaper products for children and adults, and the use of superabsorbent polymers to clean up liquid spills. The problems associated with the use of such polymers in personal care applications include a wet and sticky feel and skin irritation. Additionally, it has been difficult to find a way of applying such products in the underarm area in a way that results in an aesthetically acceptable product form. It has now been found that selected water lock superabsorbent polymers in certain formulations both with and without antiperspirant or deodorant agents may be used to create superior anti-wetness products.

It is also desirable to have the ability to reduce wetness using a deodorant product. While some deodorants contain lesser amounts of antiperspirant actives, there is a segment of the population that prefers to use deodorants that do not contain antiperspirant actives. It would be advantageous to provide a product that reduces wetness without the use of antiperspirant actives.

BRIEF SUMMARY OF THE INVENTION

The invention comprises an underarm product suitable for use to reduce wetness under the arm. It may be viewed as providing some deodorancy effect. Optionally, a portion of an antiperspirant active may be included to provide an antiperspirant/deodorant. This underarm product may be a gelled stick or a soft gel which comprises a water lock superabsorbent polymer selected from the group consisting of starch graft homopolymers and copolymers of poly(2-propenamide-co-2-propenioic acid) sodium salt. While these homopolymers and copolymers may be used in a variety of particle sizes, it is generally believed that the smaller sizes are preferred (for example, having 95% of the particles able to go through a 60 mesh screen (comparable to a size of 250 microns)). The formulations of the invention may be made as antiperspirants and/or deodorants. In the case of antiperspirants, the products give an extra measure of protection against wetness. In the case of deodorants, the products may be made with low levels of antiperspirant active or with other agents which provide a deodorizing effect but which are not antiperspirant salts.

DETAILED DESCRIPTION OF THE INVENTION

Products formulated according to the invention comprise gelled sticks or soft gels comprising:

(a) 0.01–20 weight % (particularly 0.1–10% and more particularly 0.5–5%) of a water lock superabsorbent polymer selected from the group consisting of starch graft homopolymers and copolymers of poly(2-propenamide-co-2-propenioic acid) sodium salt;

(b) 10–88 weight % of a volatile silicone having a flash point of 100 degrees C. or less (particularly a D4–D6 cyclomethicone; and especially a D5 or D6 cyclomethicone or a combination of D5 and D6 cyclomethicones);

(c) a gelling agent selected from (i) the group consisting of 5–20 weight % siliconized polyamide (especially of the type described below) if a gelled stick is desired; and (ii) 0–5 weight % of a siliconized polyamide and 0–5% of a silicone elastomer if a soft gel is desired;

(d) 0.05–85 weight % (particularly 10–85% and, more particularly, 20–75%) of water or a water soluble organic solvent (for example, ethanol, glycerol formal (a mixture of 5-hydroxy-1,3-dioxane and 4-hydroxymethyl-1,3-dioxolane, also known as methylidinoglycerol), propylene glycol, dipropylene glycol, and polyethylene glycol);

(e) for products which are not sticks, 0.05–5 weight % (particularly 0.5–5% and, more particularly, 0.5–3) of a surfactant with a hydrophilic/lipophilic balance ("HLB value") in the range of 3–13 (for example, from 0.5–50 weight % (particularly 1–30%) of a silicone copolyol which is 10% in cyclomethicone, or its equivalent may be used for a soft gel) (stick products do not require any surfactant);

(f) 0–10 weight % (particularly 5–10%) of an antiperspirant active or an effective amount of a deodorizing agent which is not an antiperspirant active;

(g) 0–20 weight % (particularly 5–10%) of a nonvolatile silicone having a flash point greater than 100 degrees C. (for example, a dimethicone); and (h) 0–20 weight % (particularly 2–12%) of an emollient (for example, a member selected from the group consisting of C12–15 alkyl benzoate, PPG-3-myristyl ether, and polyisobutene 250).

With regard to the amount of volatile silicone used in the invention, 10–40 weight % is used for stick products; and 10–88 weight % is used for soft gels (which are typically emulsions).

Optionally, one or more other ingredients can be used such as fragrance, coloring agents, antibacterial agents, masking agents, or fillers (for example, talc).

For the antiperspirant active used in the active phase various antiperspirant active materials that can be utilized according to the present invention provided that they are soluble at a suitable concentration in the water and/or glycol component (also called the active phase). These include conventional aluminum and aluminum/zirconium salts, as well as aluminum/zirconium salts complexed with a neutral amino acid such as glycine ("gly"), as known in the art. See each of European Patent Application Number 512,770 A1 and PCT case WO 92/19221, the contents of each of which are incorporated herein by reference in their entirety, for disclosure of antiperspirant active materials. The antiperspirant active materials disclosed therein, including the acidic antiperspirant materials, can be incorporated in the compositions of the present invention if they are soluble in the active phase. Suitable materials include (but are not limited to) aluminum chlorohydroxide, aluminum chloride, aluminum sesquichlorohydroxide, zirconyl hydroxychloride, and aluminum chlorohydrol-propylene glycol complex. These include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, aluminum dichlorohydrex PEG, aluminum zirconium trichlorohydrex gly propylene glycol complex, aluminum zirconium trichlorohydrex gly dipropylene glycol complex, aluminum zirconium tetrachlorohydrex gly propylene glycol complex, aluminum zirconium tetrachlorohydrex gly dipropylene glycol complex, and mixtures of any of the foregoing. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as tin or titanium analogues of the aluminum slats listed above, aluminum nitratohydrate and its combination with zirconyl hydroxychlorides and nitrates, or aluminum-stannous chlorohydrates, can be incorporated as an antiperspirant active ingredient in antiperspirant compositions according to the present invention. Preferred antiperspirant actives that can be incorporated in the compositions of the present invention include the enhanced efficacy aluminum salts and the enhanced efficacy zirconium/aluminum salt-glycine materials, having enhanced efficacy due to improved molecular distribution, known in the art and discussed, for example, in PCT No. WO92/19221, the contents of which are incorporated by reference in their entirety herein.

Antiperspirant actives can be incorporated into compositions according to the present invention in amounts in the range of 0–10% (on an anhydrous solids basis), preferably 5–10%, by weight, of the total weight of the composition. The amount used will depend on the formulation of the composition. For example, at amounts in the lower end of the broader range (for example, 0.1–5%), the antiperspirant active material will not substantially reduce the flow of perspiration, but will reduce malodor, for example, by acting as a deodorant material, for example, by acting as an antimicrobial or complexing with the malodorous components of human perspiration. Deodorant active materials can include lesser amounts of antiperspirant actives, such as in the range of 0.1–5%, as well as fragrances, and effective amounts of antimicrobial agents, for example, bacteriostatic quaternary ammonium compounds (such as cetyl trimethylammonium bromide, and cetyl pyridinium chloride), 2,4,4'-trichloro-2'-hydroxydiphenylether (Triclosan), N-(4-chlorophenyl)-N'-(3,4-dichlorophenyl)urea (Triclocarban), silver halides, octoxyglycerin (SENSIVA™ SC 50) and various zinc salts (for example, zinc ricinoleate) may also be included in formulations of the present invention. The bacteriostat can, illustratively, be included in the composition in an amount of 0.01–5.0% by weight, of the total weight of the composition. Triclosan or Triclocarban can, illustratively, be included in an amount of from 0.05% to about 5.0% by weight, of the total weight of the composition.

Gelling agents include elastomers such as (a) a dimethicone/vinyldimethicone crosspolymer composition made by reacting (in the presence of a platinum catalyst) a polymethylhydrogensiloxane with an alpha, omega-divinylpolydimethyl siloxane for which the dimethicone/vinyldimethicone crosspolymer composition (1) is used at a concentration of 4–10% in cyclomethicone (particularly 4–7%, and, more particularly, 4–6.5%) (for example, where the cyclomethicone is a D4 or D5 cyclomethicone), (2) has a refractive index in the range of 1.392–1.402 at 25 degrees C., and (3) has a viscosity in the range of 0.013–1 ×10⁴ Pascal seconds; for example, one particular elastomer of interest is KSG-15 silicone elastomer from Shin-Etsu Silicones of America (Akron, Ohio).

(b) a cyclomethicone (and) dimethicone crosspolymer made with an =Si—H containing polysiloxane and an alpha, omega-diene of formula $CH_2$=$CH(CH_2)_xCH$=$CH_2$, where x=1–20, to form a gel by crosslinking and addition of =Si—H across double bonds in the alpha, omega diene, which crosspolymer has a viscosity in the range of 50,000–3,000,000 centipoise (particularly 100,000–1,000,000; more particularly 250,000–450,000 centipoise; and most particularly 350,000 centipoise), preferably with a nonvolatiles content of 8–18% (particularly 10–14% and most particularly 12–13%) in cyclomethicone (for example a D4 or D5 cyclomethicone), (an example of such a crosspolymer composition being DC-9040 from Dow Corning Corporation (Midland, Mich.) with other types of such crosspolymers (also called elastomers) being described in U.S. Pat. No. 5,654,362, incorporated by reference herein as to the description of such polymers and methods of making such polymers). Elastomers may be used for the soft gels and are not preferred for the stick products.

Particular examples of suitable elastomers are SFE 167, a cetearyl dimethicone/vinyl dimethicone crosspolymer from GE Silicones (Waterford, N.Y.); SFE168, a cyclomethicone (and) dimethicone/vinyl dimethicone crosspolymer from GE Silicones; vinyl dimethicone crosspolymers such as those available from Shin Etsu Silicones of America (Akron, Ohio) under trade names KSG-15 (cyclomethicone (and) dimethicone/vinyl dimethicone crosspolymer), KSG-16 (dimethicone (and) dimethicone/vinyl dimethicone crosspolymer), KSG-17 (cyclomethicone (and) dimethicone/vinyl dimethicone crosspolymer), KSG-18 (phenyl trimethicone (and) dimethicone/phenyl vinyl dimethicone crosspolymer); and KSG-20 (dimethicone copolyol crosspolymer; dimethicone/vinyl dimethicone crosspolymer from Dow Corning Corporation (Midland, Mich.) under trade name Dow Corning 9506 Cosmetic Powder, DC-9040 elastomer in cyclomethicone from Dow Corning; and a mixture of cyclomethicone and stearyl-vinyl/hydromethylsiloxane copolymer available from Grant Industries, Inc. (Elmwood Park, N.J.) under the trade name Gransil SR-CYC.

For gelling agents which are polyamides, one should include at least one siliconized polyamide of Formula ULA:

Formula IIIA

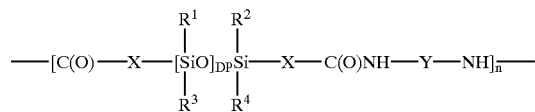

where:
(1) DP is a number in the range of 10–40 (particularly 15–30);
(2) n is a number selected from the group consisting of 1–500;
(3) X is a linear or branched chain alkylene having 1–30 carbons;

(4) Y is selected from the group consisting of linear and branched chain alkylenes having 1–40 carbons, wherein:
   (A) the alkylene group may optionally and additionally contain in the alkylene portion at least one of the members of a group consisting of (i) 1–3 amide linkages; (ii) C5 or C6 cycloalkane (as a cycloalkylene linkage); and (iii) phenylene optionally substituted by 1–3 members selected independently from the group consisting of C1–C3 alkyls; and
   (B) the alkylene group itself may optionally be substituted by at least one member selected from the group consisting of (i) hydroxy; (ii) C3–C8 cycloalkane; (iii) 1–3 members selected independently from the group consisting of C1–C3 alkyls; phenyl optionally substituted by 1–3 members selected independently from the group consisting of C1–C3 alkyls; (iv) C1–C3 alkyl hydroxy; and (v) C1–C6 alkyl amine; or Y=$Z^2$ where

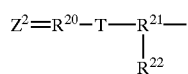

wherein each of $R^{20}$, $R^{21}$ and $R^{22}$ are independently selected from the group consisting of linear and branched C1–C10 alkylenes; and T is selected from the group consisting of (i) a trivalent atom selected from N, P and Al; and (ii) —CR, where R is selected from the group consisting of hydrogen, methyl, ethyl, propyl, isopropyl, a siloxane chain, and phenyl, wherein the phenyl may optionally be substituted by 1–3 members from the group consisting of methyl and ethyl, especially methyl and ethyl and most especially methyl; and
(5) each of $R^1$–$R^4$ is independently selected from the group consisting of methyl, ethyl, propyl, isopropyl, a siloxane chain, and phenyl, wherein the phenyl may optionally be substituted by 1–3 members from the group consisting of methyl and ethyl (with more particular values for $R^1$–$R^4$ being selected from methyl and ethyl and especially methyl);
wherein the polyamide of Formula IRA has:
   (i) a silicone portion in the acid side of the polyamide;
   (ii) a degree of polymerization in the range of 10–40 (particularly 15–30);
   (iii) an average molecular weight of at least 50,000 daltons (particularly in the range of 80,000–150,000 daltons and, more particularly in the range of 90,000–120,000 daltons) with at least 95% of the polyamide having a molecular weight greater than 10,000 daltons; and
   (iv) a polydispersity of less than 20 (particularly less than 4).

Volatile silicones and silicone surfactants are also used in the invention.

By volatile silicone material is meant a material that has a flash point of 100 degrees C. or less at atmospheric pressure. Such volatile silicones include conventional cyclic and linear volatile silicones such as cyclomethicone (especially cyclopentasiloxane, also called "D5"), "hexamethyldisiloxane", and low viscosity dimethicone (for example, Dow Corning® 200 fluid having a viscosity of 0.5–5 centistokes). Illustratively, and not by way of limitation, the volatile silicones are one or more members selected from the group consisting of cyclic polydimethylsiloxanes such as those represented by Formula III-S:

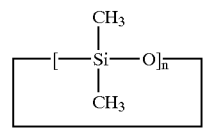

Formula III-S where n is an integer with a value of 3–7, particularly 5–6. For example, DC-245 fluid (or the DC-345 version) from Dow Corning Corporation (Midland, Mich.) is a type of cyclomethicone which can be used. These include a tetramer (or octylmethylcyclotetrasiloxane) and a pentamer (or decamethylcyclopentasiloxane). The volatile linear silicones can also be included in this group of volatile silicones and are one or more members selected from the group consisting of linear polydimethylsiloxanes such as those represented by Formula IV-S:

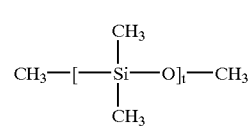

Formula IV-S and t is selected to obtain a viscosity of 0.5–5 centistokes.

Examples of such volatile silicones include one or more members selected from the group consisting of D4, D5, and D6 cyclomethicones; and linear dimethicones having a viscosity in the range of 0.5–5 centistokes. Preferably the oil phase is a mixture of one or more of D4, D5 and D6 cyclomethicones.

Suitable silicone surfactants include silicone polyglucosides (for example, octyl dimethicone ethoxy glucoside) and silicone copolyols having an BLB value (hydrophilic lipophilic balance) in the range of 3–13. A silicone copolyol (especially dimethicone copolyol) may be used in an amount of 0.05–5.0 weight % (actives basis), particularly 0.5–5.0% and, more particularly, 0.5–3.0%.

In general, silicone copolyols useful in the present invention include copolyols of the following Formulae I-S and II-S. Formula I materials may be represented by:

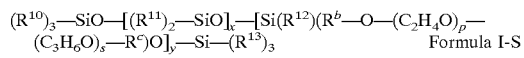

Formula I-S wherein each of $R^{10}$, $R^{11}$, $R^{12}$ and $R^{13}$ may be the same or different and each is selected from the group consisting of C1–C6 alkyl; $R^b$ is the radical —$C_mH_{2m}$—; $R_c$ is a terminating radical which can be hydrogen, an alkyl group of one to six carbon atoms, an ester group such as acyl, or an aryl group such as phenyl; m has a value of two to eight; p and s have values such that the oxyalkylene segment —$(C_2H_4O)_p$—$(C_3H_6O)_s$— has a molecular weight in the range of 200 to 5,000; the segment preferably having fifty to one hundred mole percent of oxyethylene units —$(C_2H_4O)_p$— and one to fifty mole percent of oxypropylene units —$(C_3H_6O)_s$—; x has a value of 8 to 400; and y has a value of 2 to 40. Preferably each of $R^{10}$, $R^{11}$, $R^{12}$ and $R^{13}$ is a methyl group; $R^c$ is H; m is preferably three or four whereby the group $R^b$ is most preferably the radical —$(CH_2)_3$—; and the values of p and s are such as to provide a molecular weight of the oxyalkylene segment —$(C_2H_4O)_p$—$(C_3H_6O)_s$— of between about 1,000 to 3,000. Most preferably p and s should each have a value of about 18 to 28.

A second siloxane polyether (copolyol) has the Formula II-S:

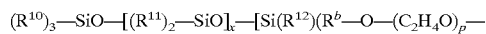

$R^c)O]_y$—Si—$(R^{13})_3$      Formula I-S wherein p has a value of 6 to 16; x has a value of 6 to 100; and y has a value of 1 to 20 and the other moieties have the same definition as defined in Formula I-S.

It should be understood that in both Formulas I and II shown above, that the siloxane-oxyalkylene copolymers of the present invention may, in alternate embodiments, take the form of endblocked polyethers in which the linking group $R_b$, the oxyalkylene segments, and the terminating radical $R^c$ occupy positions bonded to the ends of the siloxane chain, rather than being bonded to a silicon atom in the siloxane chain. Thus, one or more of the $R^{10}$, $R^{11}$, $R^{12}$ and $R^{13}$ substituents which are attached to the two terminal silicon atoms at the end of the siloxane chain can be substituted with the segment —$R^b$—O—$(C_2H_4O)_p$—$(C_3H_6O)_s$—$R^c$ or with the segment —$R^b$—O—$(C_2H_4O)_p$—$R^c$. In some instances, it may be desirable to provide the segment —$R^b$—O—$(C_2H_4O)_p$—$(C_3H_6O)_s$—$R^c$ or the segment —$R^b$—O—$(C_2H_4O)_p$—$R^c$ at locations which are in the siloxane chain as well as at locations at one or both of the siloxane chain ends.

Particular examples of suitable dimethicone copolyols are available either commercially or experimentally from a variety of suppliers including Dow Corning Corporation, Midland, Mich.; General Electric Company, Waterford, N.Y.; Witco Corp., Greenwich, Conn.; and Goldschmidt Chemical Corporation, Hopewell, Va. Examples of specific products include DOW CORNING® 5225C from Dow Corning which is a 10% dimethicone copolyol in cyclomethicone; DOW CORNING® 2-5185C which is a 45–49% dimethicone copolyol in cyclomethicone; SILWET L-7622 from Witco; ABIL EM97 from Goldschmidt which is a 85% dimethicone copolyol in D5 cyclomethicone;

and various dimethicone copolyols available either commercially or in the literature. It should also be noted that various concentrations of the dimethicone copolyols in cyclomethicone can be used. While a concentration of 10% in cyclomethicone is frequently seen commercially, other concentrations can be made by stripping off the cyclomethicone or adding additional cyclomethicone. The higher concentration materials such as DOW CORNING® 2-5185 material is of particular interest.

In one particular embodiment 0.5–50 weight % (particularly 10–30%) of a 10% silicone copolyol such as dimethicone copolyol in cyclomethicone mixture may be used, wherein the amount of mixture added is selected so that the level of silicone copolyol in the cosmetic composition is in the range of 0.05–5.0% (particularly 0.1–3.0%).

Non-volatile silicones having a flash point greater than 100 degrees C. may also be used in the formulations of this invention. Such nonvolatile silicones are those which are not under the definition of volatile silicones and include linear organo-substituted polysiloxanes which are polymers of silicon/oxygen with a general structure:

(1) $(R^{10})_3SiO(Si(R^{11})_2O)_xSi(R^{12})_3$ where $R^{10}$, $R^{11}$, $R^{12}$ can be the same or different and are each independently selected from the group consisting of phenyl and C1–C60 alkyl; or (2) $HO(R^{14})_2SiO(Si(R^{15})_2O)_xSi(R^{16})_2OH$, where $R^{14}$, $R^{14}$, $R^{15}$, $R^{16}$ can be the same or different and are each independently selected from the group consisting of phenyl and C1–C60 alkyl.

Specific examples include dimethicone, dimethiconol behenate, $C_{30-45}$ alkyl methicone, stearoxytrimethylsilane, phenyl trimethicone and stearyl dimethicone.

Emollients are a known class of materials in this art, imparting a soothing effect to the skin. These are ingredients which help to maintain the soft, smooth, and pliable appearance of the skin. Emollients are also known to reduce whitening on the skin and/or improve aesthetics. Examples of chemical classes from which suitable emollients can be found include:

(a) fats and oils which are the glyceryl esters of fatty acids, or triglycerides, normally found in animal and plant tissues, including those which have been hydrogenated to reduce or eliminate unsaturation. Also included are synthetically prepared esters of glycerin and fatty acids. Isolated and purified fatty acids can be esterified with glycerin to yield mono-, di-, and triglycerides. These are relatively pure fats which differ only slightly from the fats and oils found in nature. The general structure may be represented by Formula III:

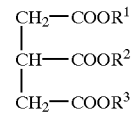

Formula III wherein each of $R^1$, $R^2$, and $R^3$ may be the same or different and each have a carbon chain length (saturated or unsaturated) of 7 to 25. Specific examples include peanut oil, sesame oil, avocado oil, coconut, cocoa butter, almond oil, safflower oil, corn oil, cotton seed oil, castor oil, hydrogenated castor oil, olive oil, jojoba oil, cod liver oil, palm oil, soybean oil, wheat germ oil, linseed oil, and sunflower seed oil;

(b) hydrocarbons which are a group of compounds containing only carbon and hydrogen. These are derived from petrochemicals. Their structures can vary widely and include aliphatic, alicyclic and aromatic compounds which have 7–40 carbon atoms. Specific examples include paraffin, petrolatum, hydrogenated polyisobutene, and mineral oil;

(c) esters which chemically are the covalent compounds formed between acids and alcohols. Esters can be formed from almost all acids (carboxylic and inorganic) and any alcohol. Esters here are derived from carboxylic acids and an alcohol. The general structure would be $R^4CO$—$OR^5$. The total number of carbons in $R^4$ and $R^5$ combined is in the range of 7–40, and the R groups can be saturated or unsaturated, straight chained or branched or can include an aromatic structure. Specific examples include isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, $C_{12-15}$ alkyl benzoates, myreth-3 myristate, dioctyl malate, neopentyl glycol diheptanoate, neopentyl glycol dioctanoate, dipropylene glycol dibenzoate, $C_{12-15}$ alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, $C_{12-15}$ alkyl fumarate, laureth-2 benzoate, propylene glycol isoceteth-3 acetate, propylene glycol ceteth-3 acetate, octyldodecyl myristate, cetyl ricinoleate, myristyl myristate (with a particular ester of interest being $C_{12-15}$ alkyl benzoate);

(d) saturated and unsaturated fatty acids which are the carboxylic acids obtained by hydrolysis of animal or vegetable fats and oils. These have general structure R⁶COOH with the R⁶ group having 7–30 carbons and R⁶ can be straight chain or branched. Specific examples include lauric, myristic, palmitic, stearic, oleic, linoleic and behenic acid;

(e) saturated and unsaturated fatty alcohols (including guerbet alcohols) with general structure R⁷COH where R⁷ can be straight chain or branched and have 7 to carbons. Specific examples include lauryl, myristyl, cetyl, isocetyl, stearyl, isostearyl, oleyl, ricinoleyl and erucyl alcohol;

(f) lanolin and its derivatives which are a complex esterified mixture of high molecular weight esters of (hydroxylated) fatty acids with aliphatic and alicyclic alcohols and sterols. General structures would include R⁸CH₂—(OCH₂CH₂)ₙOH where R⁸ represents the fatty groups derived from lanolin and n=5 to 75 or R⁹CO—(OCH₂CH₂)ₙOH where R⁹CO— represents the fatty acids derived from lanolin and n=5 to 100. Specific examples include lanolin, lanolin oil, lanolin wax, lanolin alcohols, lanolin fatty acids, isopropyl lanolate, ethoxylated lanolin and acetylated lanolin alcohols;

(g) alkoxylated alcohols wherein the alcohol portion is selected from aliphatic alcohols having 2–18 and more particularly 4–18 carbons, and the alkylene portion is selected from the group consisting of ethylene oxide, and propylene oxide having a number of alkylene oxide units from 2–53 and, more particularly, from 2–15. Examples include cetyl glyceryl ether, isostearyl glyceryl ether, isostearyl glyceryl pentaerythrityl ether, laureth-5 butyl ether, oleyl glyceryl ether, PEG-4 ditallow ether, polyglyceryl-3 cetyl ether, polyglyceryl-4 lauryl ether, PPG-9 diglyceryl ether, and propylene glycol myristyl ether. More specific examples include PPG-14 butyl ether, PPG-53 butyl ether, laureth-5 butyl ether, and PEG-4 ditallow ether;

(h) ethers selected from the group consisting of dicapryl ether, dicetyl ether, dimethyl ether, distearyl ether, ethyl ether, isopropyl hydroxycetyl ether, methyl hexyl ether, and polyvinyl methyl ether;

(i) adipic acid blends selected from the group consisting of trimethyl pentanediol/adipic acid copolymer (LEXOREZ TL8 from Inolex, Philadelphia, Pa.), trimethyl pentanediol/adipic acid/isononanoic acid copolymer (LEXOREZ TC8), and adipic acid/diethylene glycolglycerin crosspolymer (LEXOREZ 100); and (j) mixtures and blends of two or more of the foregoing. One particular group of emollients includes C12–15 alkyl benzoate (FINSOLV TN from Finetex Inc., Elmwood Park, N.J.), medium volatility dimethicone (especially 10–350 centistoke material and more especially 10–200 centistoke material), isopropyl myristate; and neopentyl glycol diheptanoate.

Particular examples of suitable emollients include members of the group consisting of Octyloxyglycerin (SENSIVA SC50 from Schütlke Mayr, Nordstedt, Germany) (which can be used as an emollient as well as an antibacterial); ethoxylated alcohols such as steareth-2, nonoxynol-2, PPG-4-Ceteth-1; ethoxylated carboxylic acids such as PEG-4 dilaurate, PEG-2 oleate; glyceryl esters such as PEG-2 castor oil, polyglyceryl-3 oleate, glyceryl stearate; sorbitan derivatives such as sorbitan oleate; PPG-3 myristyl ether (such as WITCONOL APM from Goldschmidt); neopentyl glycol diheptanoate; PEG-8 laurate; isocetyl stearate; isostearyl isostearate; isostearyl palmitate; isostearyl alcohol; PPG-5-ceteth-20; PPG-10-cetyl ether; triethyl hexanoin; ethyl hexyl isostearate, glyceryl oleate, and isopropyl isostearate.

The emollient or emollient mixture or blend thereof incorporated in compositions according to the present invention can, illustratively, be included in amounts of 1–15%, and particularly 3–12% by weight of the total weight of the composition.

While the compositions of this invention may contain both water and a water-lock polymer of the type described above, a minimum amount of water is required, such as at least 0.05 weight %. If a clear product is required the ratio of water to water-lock polymer should be in the range of 5:1 or greater.

The compositions of this invention include gelled sticks and soft gels. The compositions of the invention may range in clarity all the way from clear to opaque to white, but are preferably clear.

For stick products, the following general amounts of ingredients may be used:

Formulation A (a) 1–20 weight % (particularly 5–10%) superabsorbent polymer as described above;
(b) 10–20 weight % of a gellant which is a siliconized polyamide of Formula IIIA;
(c) 15–35 weight % of a member selected from the group consisting of a cyclomethicone (for example, one or more of D4, D5 or D6) and dimethicones having a viscosity in the range of 0.5–1000 centistokes;
(d) 5–20 weight % of a water insoluble emollient selected from the group consisting of polyisobutene and C12–15 alkyl benzoates (such as FINSOLV TN) and PPG-3 myristyl ether;
(e) 0–5 weight % (particularly 1–3%) fragrance;
(f) 15–30 weight % water.

For soft gel products, the following general amounts of ingredients may be used:

Formulation B (a) 0.5–10 weight % superabsorbent polymer of the type described above;
(b) 10–85 weight % water and a member selected from the group consisting of a water soluble organic solvent (for example, ethanol, propylene glycol, dipropylene glycol, tripropylene glycol, glycerol formal), provided a minimum of 2.5 weight % water is included;
(c) 0–5 weight % (particularly 1–3%) fragrance;
(d) 10–80 weight % of a volatile silicone selected from the group consisting of a member selected from the group consisting of a cyclomethicone (for example, one or more of D4, D5 or D6) and dimethicones having a flash point of 100 degrees C. or less;
(e) 0–10% weight % water insoluble emollient selected from the group consisting of polyisobutene and C12–15 alkyl benzoates (such as FINSOLV TN) and PPG-3 myristyl ether;
(f) 1–10 weight % surfactants (particularly 1–5%) (for example, silicone copolyols (for example, selected from the group consisting of DC-5185C (48% in cyclomethicone) from Dow Corning);
(g) 0–5 weight % of a siliconized polyamide of Formula IIIA or a silicone elastomer.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application values for n, m, etc. in formulas, molecular weights and degree of ethoxylation or propoxylation are averages. Temperatures are in degrees C. unless otherwise indicated. The amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., 7$^{th}$ ed. 1997).

Examples 1–3

Stick Products

A stick product of about 400 grams may be made using the ingredients listed in Table A. All of the ingredients for the oil phase except for the cyclomethicone (this includes dimethicone, PPG-3 myristyl ether, polyisobutene, polyamide, and C12–15 alkyl benzoate) are combined with mixing and heated to a temperature of about 110 degrees C. The mixture is then maintained at a temperature of about 110 degrees for about 10 minutes or until the polyamide is completely dissolved. The cyclomethicone is heated separately to a temperature of about 70 degrees C., and then separately added to the oil phase at a temperature of about 70–75 degrees C. The ingredients for the water phase (water and superabsorbent) are mixed in a separate beaker and heated to about 70 degrees C. The water phase is added to the oil phase slowly while maintaining the temperature of the complete mixture at about 80–85 degrees C. The combined mixture is then stirred at 500 rpm for about 3–4 minutes using an overhead mixer such as a Lightnin Mixer Model L1003 while maintaining the temperature between 80–85 degrees C. The fragrance is added when the mixture has cooled to about 65 degrees C. When the temperature is further cooled to about 62 degrees C., the product is poured into suitable containers such as ovoid shaped plastic containers approximately 3 cm (width at widest part of oval)×6 cm (length of base)×10 cm (height). The product is then cooled to ambient temperature.

TABLE A

| Ingredients (weight %) | Ex. 1 | Ex. 2 | Ex. 3 |
|---|---|---|---|
| Water Lock Superabsorbent, C200 | 10 | 7 | 5 |
| Dimethicone (10 cst) | 5 | 7 | 2 |
| C12–15 alkyl benzoate | 7.5 | 5 | 5 |
| Cyclomethicone 245 | 38.5 | 30 | 37 |
| Fragrance | 1 | 1 | 1 |
| PPG-3 myristyl ether | 5 | 10 | 5 |
| Water | 20 | 30 | 25 |
| Polyisobutene 250 | 5 | 0 | 5 |
| Silicone polyamide (DP = 15) | 8 | 10 | 15 |
| Total | 100 | 100 | 100 |

Examples 4–7

Gel Products

Gel products of about 300 grams each may be made by using the ingredients listed in Table B. The silicone copolyol (DC-2-5185C from Dow Corning), the PPG-3 myristyl ether, and the extra cyclomethicone are added to a first beaker. The mixture is stirred at about 500 rpm and heated to about 70 degrees. After the mixture is visually homogeneous, the superabsorbent polymer is added with stirring, followed by the silicone polyamide (if used) with stirring. The mixture is heated to about 90 degrees C. and kept at that temperature for about 10 minutes or until the polyamide is completely dissolved. The temperature of the mixture is then reduced to about 75 degrees C. The required amount of water is added to a second beaker and heated to about 75 degrees C. The water and ethanol are then added to the first beaker with continuous stirring and maintaining the temperature at about 75 degrees C. After the addition is completed the heater is turned off but the stirring is continued. Fragrance is added at the point where the temperature is down to about 65 degrees C. The material is then poured into suitable containers and cooled to room temperature.

Example 8

Gel Product

A gel product (100 grams) may be made using the types and amounts of ingredients listed in TABLE B. The silicone copolyol (DC 2-5185C from Dow Corning) and the other organic ingredients as well as the fragrance are combined in a 250 ml beaker and stirred at 500 rpm with an overhead mixer such as a Lightnin Mixer Model L1003. The water lock superabsorbent polymer is then added to the mixture during the mixing. After the polymer becomes visually uniformly dispersed, water is added slowly to the beaker while the stirrer is kept at 500 rpm. Stirring is continued for another 20 minutes. The product is then poured into suitable containers.

TABLE B

| Ingredients (weight %) | Ex. 4 | Ex. 5 | Ex. 6 | Ex. 7 | Ex. 8 |
|---|---|---|---|---|---|
| Water Lock Superabsorbent polymer, C200 | 4 | 3.5 | 8 | 0.5 | 6 |
| Water | 57 | 54.5 | 42 | 3 | 54 |
| Ethanol | 16 | 11 | 0 | 5 | — |
| Glycerol formal | — | 17 | — | 4.5 | — |
| Silicone polyamide (DP = 30) | 1 | 2 | 3 | 1 | — |
| Cyclomethicone (DC245) | 20 | 10 | 38 | 80 | 29 |
| Silicone copolyol (DC 2-5185C) | 1.0 | 1 | 2 | 5 | 5 |
| Fragrance | 1 | 1 | 1 | 1 | 1 |
| PPG-3 myristyl ether | — | — | 6 | — | 5 |
| Total | 100 | 100 | 100 | 100 | 100 |

Examples 9–11

Gel Product With Elastomer

A gel product (100 grams) may be made as in Example 8 using the types and amounts of ingredients listed in TABLE C. For these Examples, elastomer is used instead of the polyamide as the gelling agent.

TABLE C

| Ingredients (weight %) | Ex. 9 | Ex. 10 | Ex. 11 |
|---|---|---|---|
| Water Lock Superabsorbent polymer, C200 | 5 | 6 | 7.5 |
| Water | 54 | 54 | 42.5 |
| Silicone elastomer (Dow Corning DC9040) | 5 | 10 | 12.5 |
| Cyclomethicone (DC245) | 24 | 19 | 23.75 |
| Silicone copolyol (DC 2-5185C) | 5 | 5 | 6.25 |
| Fragrance | 1 | 1 | 1 |
| PPG-3 myristyl ether | 5 | 5 | 6.25 |

TABLE C-continued

| Ingredients (weight %) | Ex. 9 | Ex. 10 | Ex. 11 |
|---|---|---|---|
| Total | 100 | 100 | 100 |

What is claimed is:

1. A gelled stick or soft gel composition for reducing underarm wetness comprising:
   (a) 0.01–20 weight % selected from the group consisting of starch graft homopolymers and copolymers of poly (2-propenamide-co-2-propenioic acid) sodium salt;
   (b) 10–88 weight % of a volatile silicone;
   (c) a gelling agent selected from (i) a group consisting of 5–20 weight % siliconized polyamide if a gelled stick is formed; and (ii) 0–5 weight % of a siliconized polyamide and 0–5% of a silicone elastomer if a soft gel is formed;
   (d) 0.05–85 weight % of water or a water soluble organic solvent;
   (e) for products which are not sticks, 0.05–5 weight % of a surfactant with a hydrophilic/lipophilic balance in the range of 3–13;
   (f) 0–10 weight % of an antiperspirant active or an effective amount of a deodorizing agent which is not an antiperspirant active;
   (g) 0–20 weight % of a nonvolatile silicone; and
   (h) 0–20 weight % of an emollient.

2. A composition as claimed in claim 1 comprising 10–40 weight % of the volatile silicone and which is a stick product.

3. A composition as claimed in claim 1 comprising 10–88 weight % of the volatile silicone and which is a soft gel product.

4. A composition as claimed in claim 1 comprising 0.1–10 weight % of the water lock superabsorbent polymer.

5. A composition as claimed in claim 1 comprising 0.5–5 weight % of the water lock superabsorbent polymer.

6. A composition as claimed in claim 1 wherein the volatile silicone comprises comprising a member selected from the group consisting of a cyclomethicone and dimethicones having a flash point not exceeding 100 degrees C.

7. A composition as claimed in claim 1 wherein the gelling agent is a siliconized polyamide.

8. A composition as claimed in claim 1 wherein the water soluble organic solvent is selected from the group consisting of ethanol, glycerol formal, propylene glycol, dipropylene glycol, and polyethylene glycol.

9. A composition as claimed in claim 1 comprising:
   (a) 0.01–20 weight % of a water lock superabsorbent polymer selected from the group consisting of starch graft homopolymers and copolymers of poly(2-propenamide-co-2-propenioic acid) sodium salt;
   (b) 10–88 weight % of a volatile silicone selected from the group consisting of a D4–D6 cyclomethicones;
   (c) a gelling agent selected from (i) 5–20 weight % siliconized polyamide if a gelled stick is formed; and (ii) 0–5 weight % of a siliconized polyamide and 0–5% of a silicone elastomer if a soft gel is formed;
   (d) 0.05–85 weight % of water or a water soluble organic solvent, provided water is present in an amount of at least 0.05 weight %;
   (e) 0.05–5 weight % of a surfactant with a hydrophilic/lipophilic balance in the range of 3–13 for products which are not sticks and 0% surfactant for products that are sticks;
   (f) 0–10 weight % of an antiperspirant active or an effective amount of a deodorizing agent which is not an antiperspirant active;
   (g) 0–20 weight % of a nonvolatile silicone; and
   (h) 0–20 weight % of an emollient;
wherein the siliconized polyamide is of Formula IIIA:

Formula IIIA

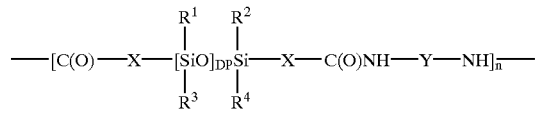

where:
(1) DP is a number in the range of 10–40;
(2) n is a number selected from the group consisting of 1–500;
(3) X is a linear or branched chain alkylene having 1–30 carbons;
(4) Y is selected from the group consisting of linear and branched chain alkylenes having 1–40 carbons, wherein:
   (A) the alkylene group may optionally and additionally contain in the alkylene portion at least one of the members of a group consisting of (i) 1–3 amide linkages; (ii) C5 or C6 cycloalkane (as a cycloalkylene linkage); and (iii) phenylene optionally substituted by 1–3 members selected independently from the group consisting of C1–C3 alkyls; and
   (B) the alkylene group itself may optionally be substituted by at least one member selected from the group consisting of (i) hydroxy; (ii) C3–C8 cycloalkane; (iii) 1–3 members selected independently from the group consisting of C1–C3 alkyls; phenyl optionally substituted by 1–3 members selected independently from the group consisting of C1–C3 alkyls; (iv) C1–C3 alkyl hydroxy; and (v) C1–C6 alkyl amine; or Y=$Z^2$ where

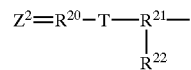

wherein each of $R^{20}$, $R^{21}$ and $R^{22}$ are independently selected from the group consisting of linear and branched C1–C10 alkylenes; and T is selected from the group consisting of (i) a trivalent atom selected from N, P and Al; and (ii) —CR, where R is selected from the group consisting of hydrogen, methyl, ethyl, propyl, isopropyl, a siloxane chain, and phenyl, wherein the phenyl may optionally be substituted by 1–3 members from the group consisting of methyl and ethyl; and
(5) each of $R^1$–$R^4$ is independently selected from the group consisting of methyl, ethyl, propyl, isopropyl, a siloxane chain, and phenyl, wherein the phenyl may optionally be substituted by 1–3 members from the group consisting of methyl and ethyl; wherein the polyamide of Formula IIIA has:
   (i) a silicone portion in the acid side of the polyamide;
   (ii) a degree of polymerization in the range of 10–40;
   (iii) an average molecular weight of at least 50,000 daltons with at least 95% of the polyamide having a molecular weight greater than 10,000 daltons; and
   (iv) a polydispersity of less than 20.

10. A composition according to claim 1 comprising 0% antiperspirant active.

11. A composition according to claim 1 comprising 5–10 weight % antiperspirant active.

12. A composition according to claim 1 comprising an effective amount of a deodorizing agent which is not an antiperspirant active.

13. A composition according to claim 1 comprising one or both of D5 and D6 cyclomethicones as the volatile silicone.

14. A composition according to claim 1 comprising a silicone elastomer as the gelling agent.

15. A composition as claimed in claim 9 wherein the polyamide of Formula IIIA has:
   (i) a silicone portion in the acid side of the polyamide;
   (ii) a degree of polymerization in the range of 15–30;
   (iii) an average molecular weight in he range of 80,000–150,000 daltons; and
   (iv) a polydispersity of less than less than 4.

16. A composition according to claim 1 comprising an emollient selected from the group consisting of
   (a) fats and oils which are the saturated or unsaturated glyceryl esters of fatty acids, or triglycerides of Formula III:

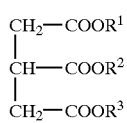

Formula III wherein each of $R^1$, $R^2$, and $R^3$ may be the same or different and each have a carbon chain length, saturated or unsaturated, of 7 to 25;
   (b) hydrocarbons containing only carbon and hydrogen and selected from aliphatic, alicyclic and aromatic compounds which have 7–40 carbon atoms;
   (c) esters of formula $R^4CO$—$OR^5$ wherein the total number of carbons in $R^4$ and $R^5$ combined is in the range of 7–40, and $R^4$ and $R^5$ can be saturated or unsaturated, straight chained or branched or can include an aromatic structure;
   (d) saturated and unsaturated fatty acids of formula $R^6COOH$ wherein $R^6$ is an alkyl group having 7–30 carbons and can be straight chain or branched;
   (e) saturated and unsaturated fatty alcohols of formula $R^7COH$ wherein $R^7$ can be straight chain or branched and has 7 to 30 carbons;
   (f) lanolin and its derivatives of formula $R^8CH_2$—$(OCH_2CH_2)_nOH$ where $R^8$ is a fatty group derived from lanolin and n=5 to 75 or formula $R^9CO$—$(OCH_2CH_2)_nOH$ where $R^9CO$— is a fatty acid group derived from lanolin and n=5 to 100;
   (g) alkoxylated alcohols wherein the alcohol portion is selected from aliphatic alcohols having 2–18 carbons, and the alkylene portion has a number of alkylene oxide units from 2–53 and is selected from the group consisting of ethylene oxide and propylene oxide;
   (h) ethers selected from the group consisting of dicapryl ether, dicetyl ether, dimethyl ether, distearyl ether, ethyl ether, isopropyl hydroxycetyl ether, methyl hexyl ether, and polyvinyl methyl ether;
   (i) adipic acid blends selected from the group consisting of trimethyl pentanediol/adipic acid copolymer, trimethyl pentanediov adipic acid/isononanoic acid copolymer, and adipic acid/diethylene glycol/glycerin crosspolymer; and
   (j) mixtures and blends of two or more of the foregoing.

17. A composition according to claim 1 comprising an emollient selected from the group consisting of C12–15 alkyl benzoate, PPG-3-myristyl ether, and polyisobutene 250.

18. A composition made by combining the ingredients listed in claim 1.

19. A composition made by combining the ingredients listed in claim 9.

20. A composition as claimed in any one of claims 1, 2, or 4–13 wherein the composition is clear.

* * * * *

UNITED STATES PATENT AND TRADEMARK OFFICE
CERTIFICATE OF CORRECTION

| | | |
|---|---|---|
| PATENT NO. | : 6,426,062 B1 | Page 1 of 1 |
| APPLICATION NO. | : 09/971978 | |
| DATED | : July 30, 2002 | |
| INVENTOR(S) | : Suman Chopra et al. | |

It is certified that error appears in the above-identified patent and that said Letters Patent is hereby corrected as shown below:

Col. 1, line 64, delete "water lock"

Col. 10, line 10, "water lock polymer of the type" should be changed to --a polymer of the type sold under the trademark WATER LOCK®, registered trademark of Grain Processing Corporation, Muscatine, Iowa, for high-absorbent polymers.--

Col. 11, Table A: "Water Lock" should be changed to --WATER LOCK®--

Col. 12, Table B: "Water Lock" should be changed to --WATER LOCK®--

Col. 12, Table C: "Water Lock" should be changed to --WATER LOCK®--

Signed and Sealed this

Seventeenth Day of July, 2007

JON W. DUDAS
*Director of the United States Patent and Trademark Office*